United States Patent
Wang (10) Patent No.: US 7,491,414 B2
(45) Date of Patent: Feb. 17, 2009

(54) **ANTI-INFLAMMATORY SUBSTANCES EXTRACTED FROM *ECHINACEA***

(75) Inventor: Xiping Wang, Brevard, NC (US)

(73) Assignee: Gaia Herbs, Inc., Brevard, NC (US)

( * ) Notice: Subject to any disclaimer, the term of this patent is extended or adjusted under 35 U.S.C. 154(b) by 70 days.

(21) Appl. No.: 11/248,517

(22) Filed: Oct. 12, 2005

(65) Prior Publication Data

US 2007/0082074 A1    Apr. 12, 2007

(51) Int. Cl.
*A61K 36/28* (2006.01)

(52) U.S. Cl. ...................................... 424/737

(58) Field of Classification Search ............... None
See application file for complete search history.

(56) References Cited

U.S. PATENT DOCUMENTS

| | | | |
|---|---|---|---|
| 5,176,913 A | 1/1993 | Honerlagen et al. | |
| 6,238,696 B1 | 5/2001 | Wang | |
| 6,251,926 B1 * | 6/2001 | Momose et al. | 514/364 |
| 6,261,565 B1 | 7/2001 | Empie et al. | |
| 6,447,815 B1 | 9/2002 | Menon et al. | |
| 6,482,432 B2 | 11/2002 | Wang | |
| 6,511,683 B1 | 1/2003 | Gahler et al. | |
| 6,991,811 B1 * | 1/2006 | Brovelli et al. | 424/725 |
| 2002/0028258 A1 | 3/2002 | Mitscher et al. | |
| 2004/0022878 A1 | 2/2004 | Giori et al. | |
| 2004/0151789 A1 | 8/2004 | Levine et al. | |

FOREIGN PATENT DOCUMENTS

| | | | |
|---|---|---|---|
| CH | 688787 | * | 3/1998 |
| DE | 3744571 A | * | 12/1987 |
| DE | 37 44 571 A1 | | 7/1989 |
| DE | 3744571 | * | 7/1989 |
| EP | 0 464 298 | | 6/1995 |
| WO | WO 99/21007 A1 | | 5/1999 |
| WO | WO 2005/053720 A1 | | 6/2005 |

OTHER PUBLICATIONS

Goel et al. "Alkylamides of *Echinacea purpurea* Stimulate Alveolar Macrophage Function in Normal Rats" *International Immunopharmacology* 2: 381-387 (2002).
Bauer et al. "TLC and HPLC Analysis of Alkamides in *Echinacea* Drugs" *Planta Medica* 55:367-371 (1989).
Binns et al. "Phytochemical Variation in *Echinacea* from Roots and flowerheads of Wild and Cultivated Populations" *J. Agric. Food chem.*. 50:3673-3687 (2002).
Dietz et al. "The Constituents of *Echinacea atrorubens* Roots and Aerial Parts" *Pharmaceutical Biology* 39(1):11-15 (2001).
He et al. "Analysis of alkamides in roots and achenes of *Echinacea purpurea* by liquid chromatography-electrospray mass spectrometry" *Journal of Chromatography A* 815:205-211 (1998).
International Search Report and Written Opinion for PCT/US2006/036565; date of mailing Jul. 23, 2007.
Kraus et al. "Synthesis and Natural Distribution of Anti-inflammatory Alkamides from *Echinacea*" *Molecules* 11:758-767 (2006).
Mølgaard et al. "HPLC Method Validated for the Simultaneous Analysis of Cichoric Acid and Alkamides in *Echinacea purpurea* Plants and Products" *J. Agric. Food Chem.* 51:6922-6933 (2003).

* cited by examiner

*Primary Examiner*—Christopher R. Tate
(74) *Attorney, Agent, or Firm*—Myers Bigel Sibley & Sajovec, P.A.

(57) ABSTRACT

An *Echinacea* composition containing the immunosuppressive components of an *Echinacea* extract but not the immunostimulatory components is disclosed. A process for isolating *Echinacea* immunosuppressive components by extraction with lipophilic compounds is also disclosed. The *Echinacea* composition can be used for treatment of colds, flu, and other upper respiratory tract infections, inflammatory diseases, and immunomodulatory disorders.

8 Claims, 8 Drawing Sheets

ANTI-INFLAMMATORY SUBSTANCES EXTRACTED FROM *ECHINACEA*

GOVERNMENT SUPPORT

The present invention was made, in part, with the support of grant number R44 ATO 0771 from the National Center for Complementary and Alternative Medicine, National Institutes of Health. The United States Government may have certain rights in the invention.

FIELD OF INVENTION

The present invention relates to a composition prepared from Echinacea plant material in which the composition has high anti-inflammatory and immunosuppressive activity and low or no immunostimulatory activity, and methods for the preparation of such a composition. The anti-inflammatory and immunosuppressive Echinacea composition of the present invention can be used for treatment of colds, flu, and other upper respiratory tract infections, inflammatory diseases, and immunomodulatory disorders.

BACKGROUND OF THE INVENTION

Echinacea plants have been used medicinally for many years and today, Echinacea preparations are sold worldwide. Various methods for the isolation of these compounds have been used including, for example, extraction with organic solvents, and isolation by column chromatography and thin layer chromatography. However, none of the processes developed so far are suitable for production scale manufacturing. Furthermore, up until recently, the quality and efficacy of Echinacea preparations has been unreliable and research results using them have been contradictory. For example, some researchers have reported that alkamides (also referred to as alkylamides or isobutylamides) have immunostimulatory activity (Y. Goel et al., Alkylamides of *Echinacea purpurea* stimulate alveolar macrophage function in normal rats. *International Immunopharmacology* 2:381-387 (2002)), while others report alkamides to have immunosuppressive activity in vitro as evidence by the inhibition of cyclooxygenase and 5-lipoxystimulatory activities (B. Muller-Jakic et al., In vitro inhibition of cyclooxygenase and 5-lipoxygenase by alkamides from *Echinacea* and *Achillea* species. *Planta Medica* 60:37-40 (1994); R. Bauer et al., Echinacea species as potential immunostimulatory drugs. *Economic and Medicinal Plant Research* 5:253-321 (1991)).

Commercially available *Echinacea* products are typically found to have both immunosuppressive and immunostimulatory components. For example, the preparations disclosed in U.S. Pat. Nos. 6,511,683 and 6,447,815 contain both bioactive components. U.S. Pat. No. 6,511,683, proposes to provide compositions composed of *Echinacea polysaccharides*, *Echinacea* alkylamides and cichoric acid and methods for preparing such compositions. This patent also proposes to provide compositions enriched in at least one *Echinacea* component. The method involves selecting *Echinacea* plants at a particular stage of development having an enhanced amount of desired component and further selecting a portion of the plant that is enriched in the desired component. However, the method of extraction remains the same and the extracts continue to have both immunostimulatory and immunosuppressive components. U.S. Pat. No. 6,447,815, proposes a method of extracting herbs and plant material including *Echinacea* wherein higher yields of marker compounds such as alkamides, may be obtained. However, *Echinacea* compositions prepared by this method are found to contain both immunostimulatory and immunosuppressive components.

Currently, there remains a need to provide a method of producing preparations of *Echinacea* anti-inflammatory and immunosuppressive components including alkamides, which do not also contain immunostimulatory components. The present invention discloses a method of preparing an *Echinacea* composition at a production scale level that contains only the anti-inflammatory and immunosuppressive components such as the alkamides, polyacetylenes and fatty acids and does not contain the immunostimulatory components such as cichoric acid, echinacoside, polysaccharides and glycoproteins. The methods of this invention produce an *Echinacea* composition having anti-inflammatory and immunosuppressive activity that can be used, for example, for the treatment of colds, flu, and other upper respiratory tract infections, inflammatory diseases and immunomodulatory disorders.

SUMMARY OF THE INVENTION

The present invention provides a process for isolating anti-inflammatory and immunosuppressive alkamides from *Echinacea* plant material in which the final preparation contains the anti-inflammatory and immunosuppressive lipophilic alkamide components but not the immunostimulatory hydrophilic components. Furthermore, the process disclosed is readily adaptable to large-scale production of *Echinacea* anti-inflammatory and immunosuppressive compounds. One embodiment of the process comprises the steps of (a) extracting the *Echinacea* plant material, for example, with an alcohol, to provide an *Echinacea* concentrate; (b) extracting the *Echinacea* concentrate with a lipophilic compound to provide a lipophilic portion containing the anti-inflammatory and immunosuppressive alkamides and a hydrophilic portion; and (c) separating the hydrophilic portion from the lipophilic portion to provide a remaining lipophilic portion having a concentration of *Echinacea* anti-inflammatory and immunosuppressive alkamides from 0.5 percent to 50 percent w/w. The remaining lipophilic portion, once separated from the hydrophilic portion, can be washed with water to reduce further any remaining hydrophilic compounds.

An additional embodiment of the invention provides a composition comprising a fraction having 0.5 to 50 percent anti-inflammatory and immunosuppressive alkamides prepared by subjecting *Echinacea* plant material to conditions sufficient to provide an *Echinacea* concentrate; extracting the *Echinacea* concentrate with a lipophilic compound to provide a lipophilic portion containing the anti-inflammatory and immunosuppressive alkamides and a hydrophilic portion; and separating the hydrophilic portion from the lipophilic portion to provide a remaining lipophilic portion having a concentration of *Echinacea* anti-inflammatory and immunosuppressive alkamides from 0.5 percent to 50 percent w/w.

The *Echinacea* composition of the invention may be used alone or in combination with other plant extracts or with other dietary supplements such as vitamins and minerals, etc., to provide a nutritional supplement optimized for a desired health effect.

DETAILED DESCRIPTION OF THE INVENTION

In the following detailed description, embodiments of the present invention are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

Unless otherwise defined, all technical and scientific terms used herein have the same meaning as commonly understood by one of ordinary skill in the art to which this invention belongs.

DEFINITIONS

*Echinacea* plant material includes all *Echinacea* species, cultivars and varieties and can be selected from the group including, but not limited to, *Echinacea angustifolia, Echinacea purpurea, Echinacea pallida, Echinacea atrorubens, Echinacea laevigata, Echinacea sanguinea, Echinacea simulata*, and *Echinacea tennesseensis*.

"Alcohol" includes, but is not limited to, methanol, ethanol, isopropanol, propanol, isobutanol, and butanol.

"Lipophilic compound" includes, but is not limited to, vegetable oil, lecithin and lipophilic organic solvents.

"Vegetable oil" includes, but is not limited to, olive oil, canola oil, safflower oil, sunflower oil, peanut oil, corn oil, soybean oil, sesame oil, any other food grade vegetable source oil and mixtures thereof.

"Lipophilic organic solvent" includes, but is not limited to, chloroform, ethyl acetate, petroleum, hexane, polyethylene glycol and dichloromethane.

"Water" includes, but is not limited to, deionized water, spring water, distilled water, tap water and well water.

"Anti-inflammatory" and "immunosuppressive" means the biologically active properties of alkamides and/or the lipophilic extracts from *Echinacea* plants. "Anti-inflammatory" and "immunosuppressive" can be used separately or together when the bioactive properties of alkamides or lipophilic extracts are described herein.

As summarized above, the present invention provides a process by which *Echinacea* extracts can be prepared that contain the anti-inflammatory and immunosuppresive components but not the immunostimulatory components. Furthermore, the process disclosed is readily adapted to large scale production of *Echinacea* anti-inflammatory and immunosuppresive components.

In accordance with the present invention, an extract of *Echinacea* plants is prepared. The species, cultivar or variety of *Echinacea* that can be used includes, but is not limited to, *Echinacea angustifolia, Echinacea purpurea, Echinacea pallida, Echinacea atrorubens, Echinacea laevigata, Echinacea sanguinea, Echinacea simulata*, and *Echinacea tennesseensis*. In addition, the plant material used in the extraction can be any part of the plant and includes, but is not limited to, the root, leaf, flower, fruit, seed, and stem. Preferably, the plant material used is the root. The plant material can be fresh or dried and can be organically cultivated, not organically cultivated or it can be wild crafted (grown in the wild).

In the present invention, the *Echinacea* plant material may be extracted by any process sufficient to produce an *Echinacea* concentrate. In one embodiment of the invention, the plant material is first ground or cut-up prior to extraction. If the plant material is fresh, the material can be extracted with alcohol. In one embodiment, the alcohol used is ethanol. Alternatively, if the plant material is dried, it can be extracted with an alcohol-water mixture. In one embodiment, the alcohol is a 70 percent mixture of ethanol to water. The extraction method can be, but is not limited to, maceration, percolation, or ultrasonic extraction. The temperature used during the extraction process can be anywhere between 4° C. to 70° C. Furthermore, the alcohol extraction can be repeated one or more times. The *Echinacea* extract can be filtered to remove any particulate matter. The concentrate is condensed to remove most of the alcohol using techniques known in the art.

The resultant *Echinacea* concentrate can be extracted with a lipophilic compound or organic solvent. The lipophilic compound includes, but is not limited to, vegetable oil, lecithin and lipophilic organic solvents. In one embodiment, the lipophilic compound is olive oil. The extraction of the *Echinacea* concentrate with a lipophilic compound results in a lipophilic portion containing the anti-inflammatory and immunosuppressive components such as alkamides and other lipophilic components and a hydrophilic portion containing immunostimulatory components such as cichoric acid, echinacoside, polysaccharides and glycoproteins. The lipophilic anti-inflammatory and immunosuppressive portion and the hydrophilic portion are separated using techniques known in the art.

The resultant anti-inflammatory and lipophilic immunosuppressive portion is washed with water to remove any remaining hydrophilic components. High pressure liquid chromatographic analysis of the final lipophilic portion, for example, shows a total concentration of anti-inflammatory and immunosuppressive alkamides from 0.5 percent to 50 percent by w/w.

The *Echinacea* lipophilic anti-inflammatory and immunosuppressive composition of this invention can be administered orally for use as a treatment of colds, flu, and other upper respiratory tract infections, inflammatory diseases, and immunomodulatory disorders. The *Echinacea* anti-inflammatory and immunosuppressive composition can be prepared in liquid form such as an ethanol-based liquid, oil-based capsules and soft gel capsules, and dry powder forms such as tablets, two piece hard shell capsules, and soft gel capsules with different carriers, the selection of which will be within the skill of one in the art.

The following Examples are provided to illustrate various embodiments of the present invention but are not meant to limit the embodiments of the present invention in any way.

EXAMPLES

Example 1

Preparation from Fresh Echinacea Material Using Olive Oil

Four and one-half kilograms of fresh *Echinacea purpurea* root was washed with tap water and cut into small pieces (2-5 mm) with a cutting mill. The *Echinacea purpurea* root pieces were then mixed with four and one-half kilograms of fresh *Echinacea angustifolia* root (with 75 percent moisture) and ground in a Vibratory Centrifugal mill (VCM) for 5 min. Twenty-five and eight tenths liter of 95 percent ethanol and 2.7 L de-ionized water were added. The mixture was then ground for an additional 20 min and the liquid collected. The ground material was removed from the VCM and pressed with a hydraulic press. The liquid from the pressed material was combined with the previously collected liquid and filtered first through a 100 μm screen filter and then a 10 μm screen filter. The total filtrate volume was 28 L. The filtrate was then condensed at 40° C. under reduced pressure to remove the most of the ethanol. 5 L of concentrate was obtained.

The concentrate was placed into a 15 L separatory funnel and 4 L of olive oil was added. The mixture was stirred for 5 min and then allowed to separate into two layers, a bottom hydrophilic layer and an upper lipophilic or olive oil layer. The bottom hydrophilic layer was drained out through a bottom opening and the lipophilic layer was poured out through a top opening. The hydrophilic layer was again placed into the separatory funnel and extracted once more with an additional 4 L of fresh olive oil. The mixture was stirred for 5 min, and then allowed to separate into two layers, a bottom hydrophilic layer and an upper lipophilic or olive oil layer. The bottom hydrophilic layer was drained out through the bottom opening and the lipophilic layer was poured out through the top opening. The extraction procedure was repeated one more time.

The lipophilic layers were combined and placed into a separatory funnel. Five liters of deionized water was added and the mixture was stirred for 5 min. The mixture was then allowed to separate and the bottom hydrophilic layer was drained out through the bottom opening and the top lipophilic layer collected. Total anti-inflammatory and immunosuppressive alkamide concentration in the hydrophilic layer was determined to be 3.56 percent (35.6 mg/g) using HPLC.

Figure 1:
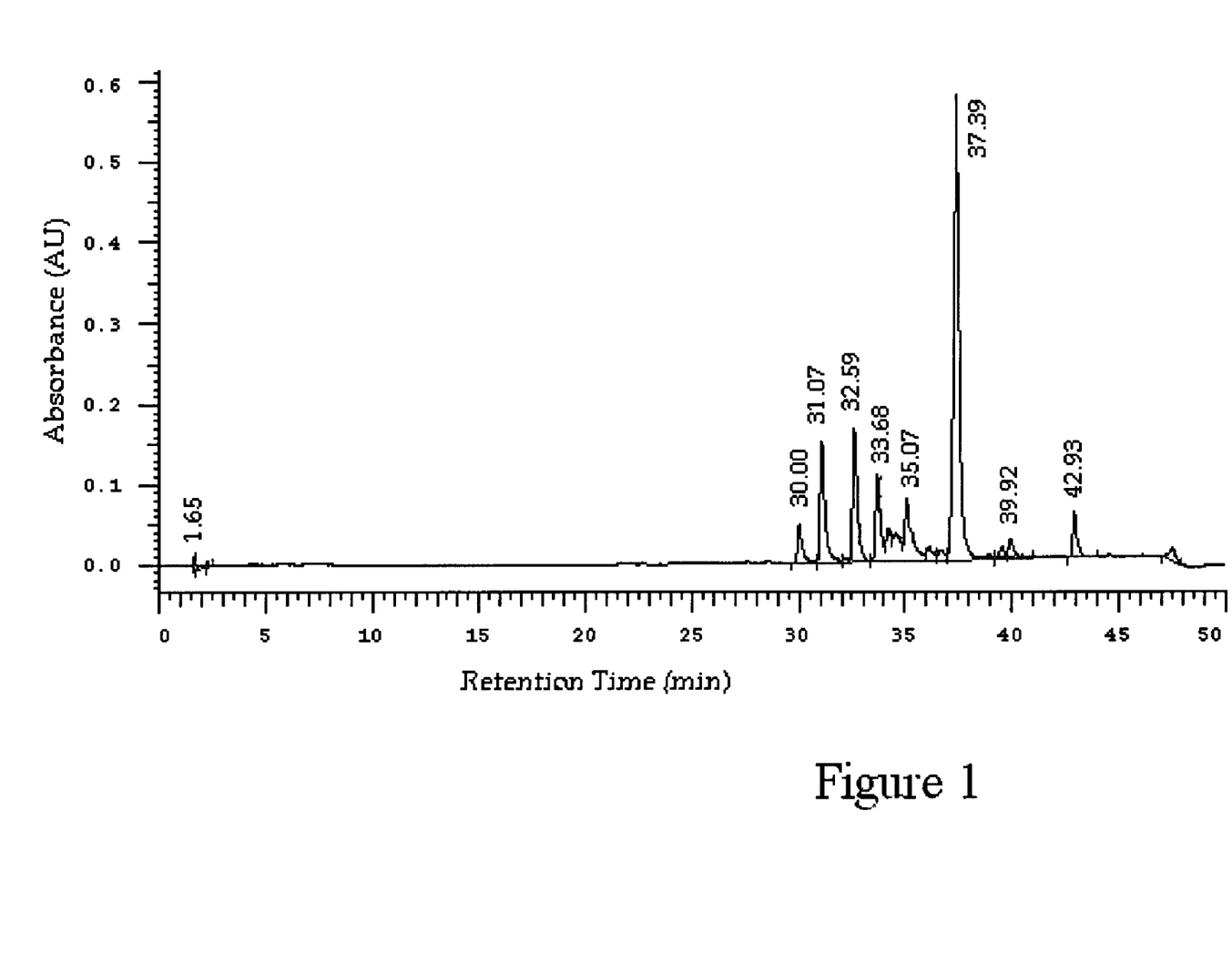
FIG. 1 is a high pressure liquid chromatography (HPLC) profile of an olive oil extract of a mixture of *Echinacea angustifolia* root and *Echinacea purpurea* root.

High pressure liquid chromatography (HPLC) profiles of extracts prepared by the olive oil extraction method outlined in the Example 1 are shown in FIG. 1. The retention times for the various compounds in FIG. 1 were Dodeca-2E,4E,8Z,10E-tetraenoic acid isobutylamide and Dodeca-2E,4E,8Z,10Z-tetraenoic acid isobutylamide at 37.17 min; no echinacoside or cichoric acid peaks were observed at retention times below 25 min (typically, these compounds would be observed at about 11 min for echinacoside and about 15 min for cichoric acid). These HPLC profiles illustrate that extraction of the Echinacea plant with olive oil allows the extraction of anti-inflammatory and immunosuppressive compounds without the immunostimulatory compounds.

Example 2

Preparation from Dried Echinacea Material Using Extra-Thin Lecithin

Nine kilograms of dry *Echinacea angustifolia* and *Echinacea purpurea* roots with 12 percent moisture was ground in hammer mill and the ground root transferred to an extractor. Thirty-six liters of 70 percent ethanol was added. The extractor was heated to 40° C. and extraction solvent circulated for 3 hours. The liquid was collected from the extractor and the root material removed and placed into a hydraulic press in order to obtain any remaining liquid. The liquid from the press was combined with the liquid collected from the extractor. The combined liquid was then filtered first through 100 μm screen and then a 10 μm screen. The total volume of the filtrate was 32 L. The filtrate was condensed at 40° C. under reduced pressure to remove most of the ethanol. Five liters of concentrate was obtained.

The concentrate was placed into a 15 L separatory funnel and 4 L of extra-thin lecithin was added. The mixture was stirred for 5 min and then allowed to separate into two layers, a lower hydrophilic layer and an upper lipophilic, lecithin layer. The lower hydrophilic layer was drained out through a bottom opening and the upper lipophilic layer was poured out through a top opening. The hydrophilic layer was again placed into the separatory funnel and extracted once more with an additional 4 L of fresh extra-thin lecithin. The mixture was stirred for 5 min, and then allowed to separate into two layers, a bottom hydrophilic layer and an upper lipophilic layer. The bottom hydrophilic layer was drained out through the bottom opening and the lipophilic layer was poured out through the top opening. The extraction procedure was repeated one more time.

The lipophilic layers were combined and placed into a separatory funnel. Five liters of deionized water was added and the mixture stirred for 5 min. After the mixture was allowed to separate into an upper lipophilic layer and a lower hydrophilic layer, the lower hydrophilic layer was drained out through the bottom opening. The upper lipophilic, lecithin layer was collected and analyzed for the concentration of total anti-inflammatory and immunosuppressive alkamides using HPLC. The concentration of the anti-inflammatory and total immunosuppressive alkamides was 4.46 percent (44.6 mg/g).

Figure 2:
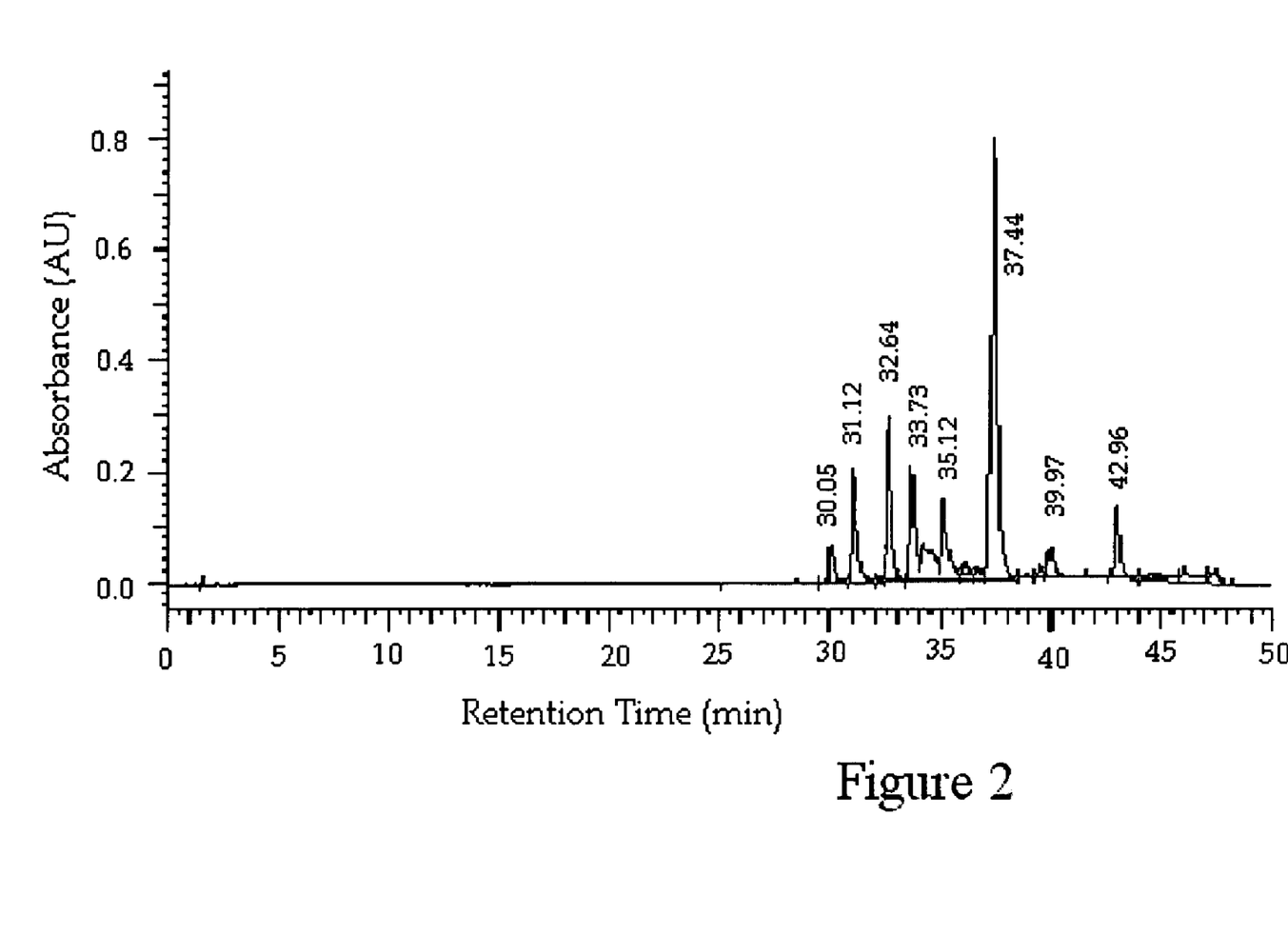
FIG. 2 is a HPLC profile of an extra-thin lecithin extract of a mixture of *Echinacea angustifolia* root and *Echinacea purpurea* root.
Figure 3:
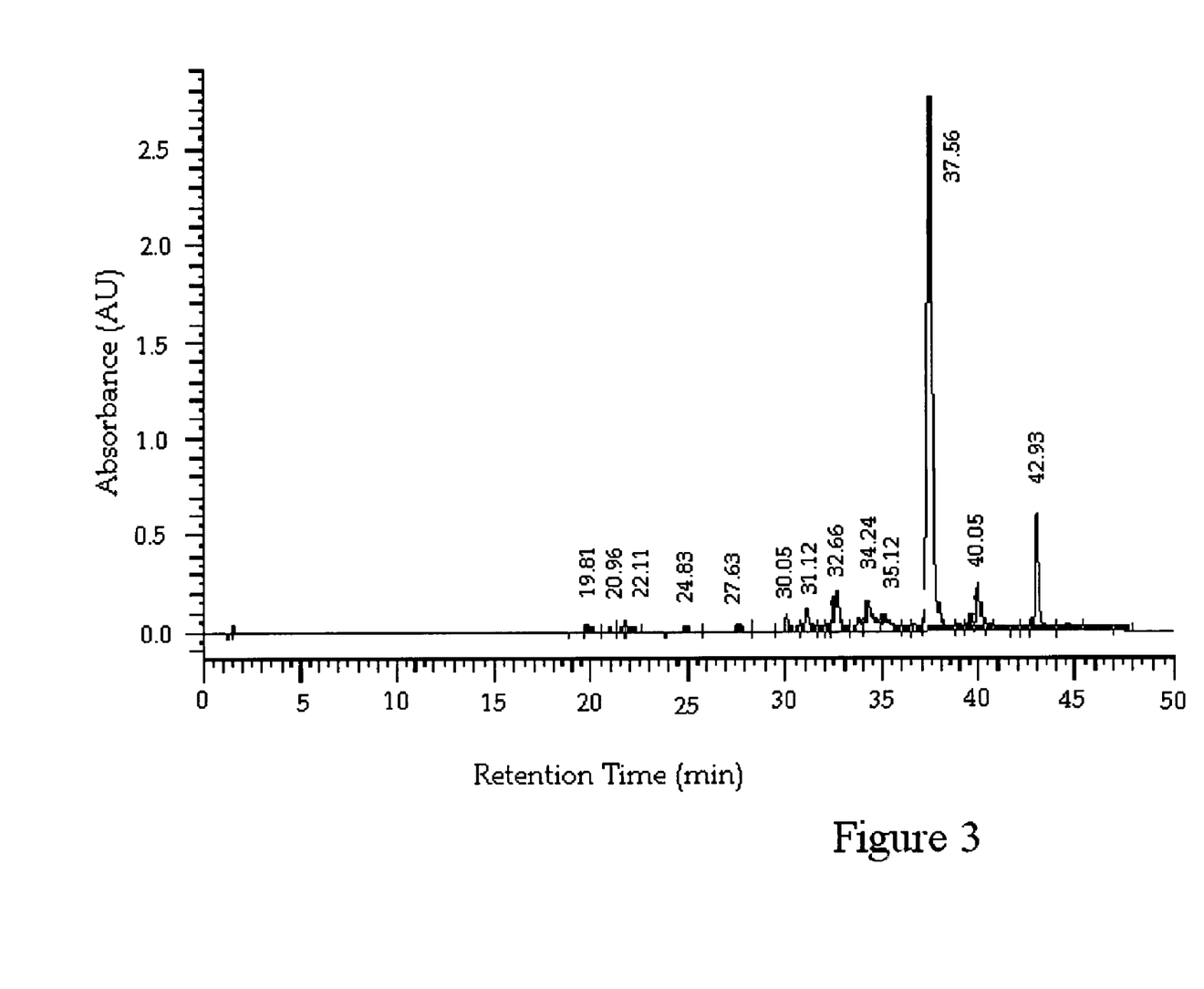
FIG. 3 is a HPLC profile of an extra-thin lecithin extract of *Echinacea angustifolia* root.

The HPLC profile of an extra-thin lecithin extract of a mixture of *Echinacea angustifolia* root and *Echinacea purpurea* root is shown in FIG. 2. The retention times of the various compounds were: Dodeca-2E,4E,8Z,10E-tetraenoic acid isobutylamide and Dodeca-2E,4E,8Z, 10Z-tetraenoic acid isobutylamide at 37.47 min. No echinacoside peaks were observed at retention times at about 11 min and no cichoric acid peaks were observed at about 15 minutes. The HPLC profile of an extra-thin lecithin extract of only *Echinacea angustifolia* root is shown in FIG. 3. Procedures used to produce this extract were the same as those outlined in this Example 2 except that only *E. angustifolia* root was used. The retention times for the various compounds were: Dodeca-2E, 4E,8Z,10E-tetraenoic acid isobutylamide and Dodeca-2E, 4E,8Z, 10Z-tetraenoic acid isobutylamide at 37.76 min. Neither of the chromatograms shown in FIG. 2 or FIG. 3 exhibited an echinacoside peak at a retention time of about 11 min or a cichoric acid peak at a retention time of about 15 min. These HPLC profiles illustrate that the procedure of the present invention using lecithin to extract the *Echinacea* plant allows the extraction of immunosuppressive compounds without the immunostimulatory compounds.

Example 3

Preparation from Dried Echinacea Material Using Organic Solvent

Nine kilograms of dry *Echinacea angustifolia* root with 9 percent moisture was ground in a hammer mill and the ground root was transferred to an extractor. Thirty-six liters of 70 percent ethanol was added to the extractor and ground root material. The extractor was heated to 40° C. and extraction solvent circulated for 3 hours. The liquid was collected from the extractor and the root material removed and placed in a hydraulic press in order to obtain any remaining liquid. The liquid from the press was combined with the liquid collected from the extractor and then filtered through a 10 μm screen. The total volume of the filtrate was 31 L. The filtrate was then condensed at 40° C. under reduced pressure to remove most of the ethanol. Seven liters of concentrate was obtained.

The 7 L of concentrate was placed in a 15 L separatory funnel and 6 L ethyl acetate added. The mixture was stirred for 5 min and then allowed to separate into two layers, a lower hydrophilic layer and an upper ethyl acetate layer. The bottom hydrophilic layer was drained out through a bottom opening and the top ethyl acetate layer poured out through a top opening.

The hydrophilic layer was again placed into the separatory funnel and extracted once more with an additional 6 L of ethyl acetate. The mixture was stirred for 5 min, and then allowed to separate into two layers, a bottom hydrophilic layer and an upper ethyl acetate layer. The bottom hydrophilic layer was drained out through the bottom opening and the ethyl acetate layer was poured out through the top opening. The extraction procedure was repeated one more time.

The ethyl acetate layers were combined and placed into a separatory funnel. Ten liters of deionized water was added and the mixture stirred for 5 min. After the mixture was allowed to separate into an upper ethyl acetate layer and a lower hydrophilic layer, the lower hydrophilic layer was drained out through the bottom opening and the upper ethyl acetate layer was collected through the top opening. The upper ethyl acetate layer was then condensed at 40° C. under reduced pressure to remove the ethyl acetate. Any remaining ethyl acetate and moisture were removed by freeze-drying overnight. The residue was removed from the flask and stored in the freezer.

Figure 4:
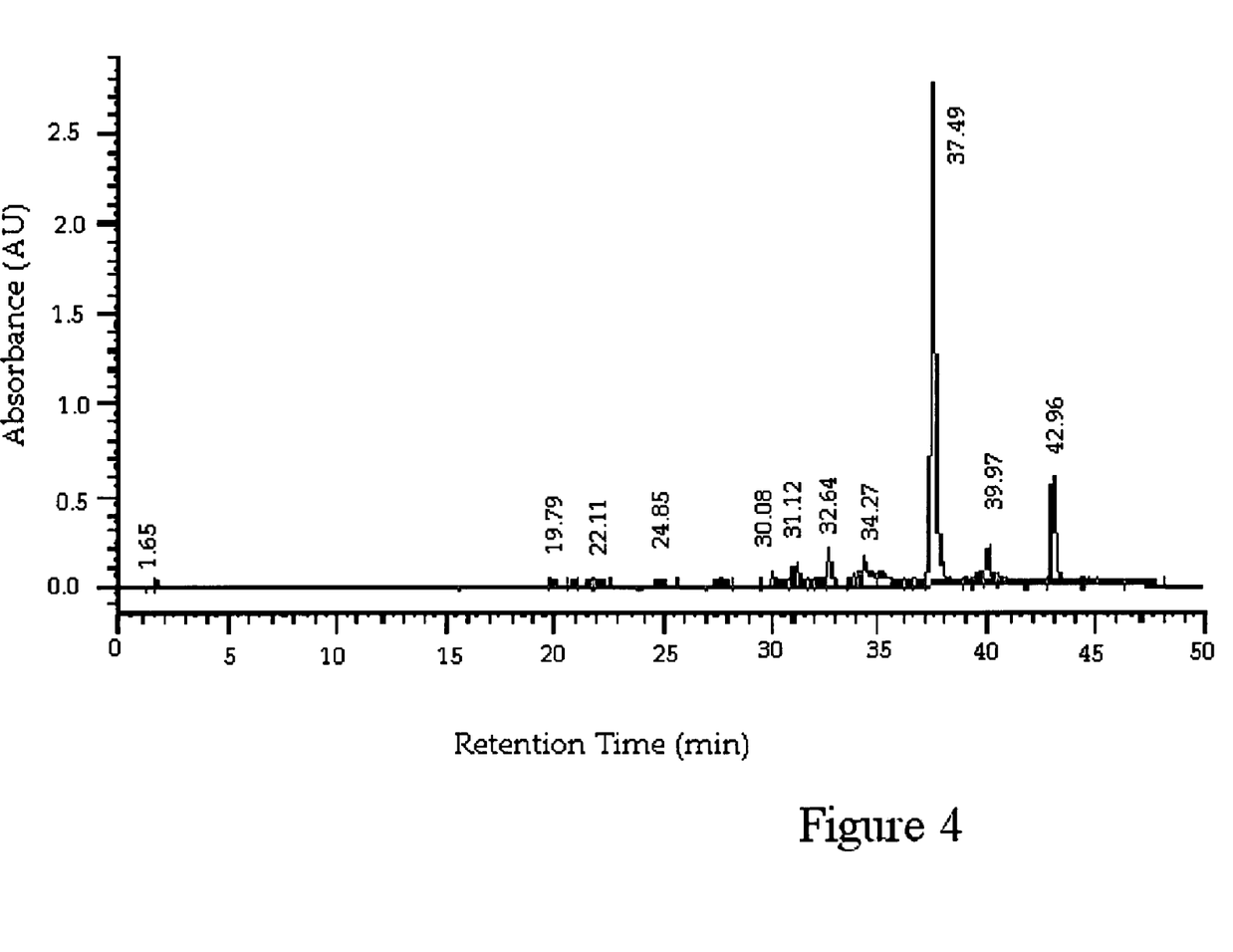
FIG. 4 is a HPLC profile of an ethyl acetate extract of *Echinacea angustifolia* root.

The concentration of total anti-inflammatory and immunosuppressive alkamides in the dried extract was 10.5 percent (105 mg/g) as determined by HPLC. The HPLC profile of an ethyl acetate extract of *Echinacea angustifolia* root is shown in FIG. 4. The retention times of the various compounds were: Dodeca-2E,4E,8Z,10E-tetraenoic acid isobutylamide and Dodeca-2E,4E,8Z, 10Z-tetraenoic acid isobutylamide at 37.44 min. No echinacoside or cichoric acid peaks were observed at retention times below 25 min (these compounds are typically observed at retention times of about 11 min for echinacoside and about 15 min for cichoric acid). The HPLC profile of FIG. 4 illustrates that extraction of the *Echinacea* plant with ethyl acetate allows the extraction of anti-inflammatory and immunosuppressive compounds without the immunostimulatory compounds.

Example 4

Immunosuppressive Bioassay

A procedure detecting nitrite oxide (NO) production was used to assay the immunomodulatory activity of the extracts. For this procedure a murine macrophage cell line Raw 264.7 was pre-incubated with various concentrations of extract for four hours and then stimulated with 5 ng/ml lipopolysaccharide (LPS) for 24 hours. In some experiments, after the pre-incubation with extract, the culture medium was removed and cells were washed several times before being subjected to LPS stimulation. The supernatant of the cultures were analyzed for nitrite production, an indicator of nitric oxide (NO) synthesis. The supernatants were mixed with Griess reagents (Promega), and their absorbance at 550 run ($A_{550}$) measured using VersaMax (Molecular Devices). The relative NO production was derived by (Exp-OD−Control-OD)/(LPS-OD−Control-OD)×100 percent. The immunosuppressive activity can be from $ID_{50}$ (median inhibitory dose) 100 μg/ml to $ID_{50}$ 0.001 ng/ml.

Example 5

High Pressure Liquid Chromatography

High pressure liquid chromatography was used to analyze the extracts. The instrument used was a Hitachi D-7000 with L-7450 diode array detector set at 260 rn. The column used was Phenomenex, Luna 150×4.6 mm, 5μ, $C_{18}$ (2). The mobile phase at 0 min comprised a mixture of 75 percent water, 5 percent methanol, 5 percent acetonitrile, and 15 percent of 0.5 percent phosphoric acid. This was followed at 45 min by a mixture comprised of 5 percent water, 40 percent methanol, 50 percent acetonitrile, and 5 percent of 0.5 percent phosphoric acid.

Example 6

Preparation of a Standardized Alkamide Extract Capsule

One thousand milliliters of a standardized anti-inflammatory and immunosuppressive alkamide lecithin extract (4.46 percent) was mixed thoroughly with 1.55 L extra-thin lecithin. The mixture was encapsulated into size "0" hydroxypropylmethyl cellulose (HPMC) two piece hard shell capsules and the capsule sealed with HPMC. Each capsule contained 0.57 ml of the mixture and was equal to 10 mg of total anti-inflammatory and immunosuppressive alkamides.

Example 7

Preparation of Standardized Alkamide Liquid Solution

Ninety-six grams of the standardized anti-inflammatory and immunosuppressive alkamide extract from Example 3 was dissolved in 1000 ml of 70 percent ethanol. The solution was packaged in 30 ml ember glass bottles with droppers. The total immunosuppressive alkamide concentration was determined to be 10 mg/mL.

Comparative Example 1

Nine kilograms of dry *Echinacea angustifolia* root and *Echinace purpurea* root, stem, leaves, and flower head with 12 percent moisture was ground in hammer mill and the ground root transferred to an extractor. Thirty-six liters of 70 percent ethanol were added. The extractor was heated to 40° C. and extraction solvent circulated for 3 hours. The liquid was collected from the extractor and the root material removed and placed into a hydraulic press in order to obtain any remaining liquid. The liquid from the press was combined with the liquid collected from the extractor. The combined liquid was then filtered first through 100 µm screen and then a 10 µm screen. The total volume of the filtrate was 32 L.

Figure 5:
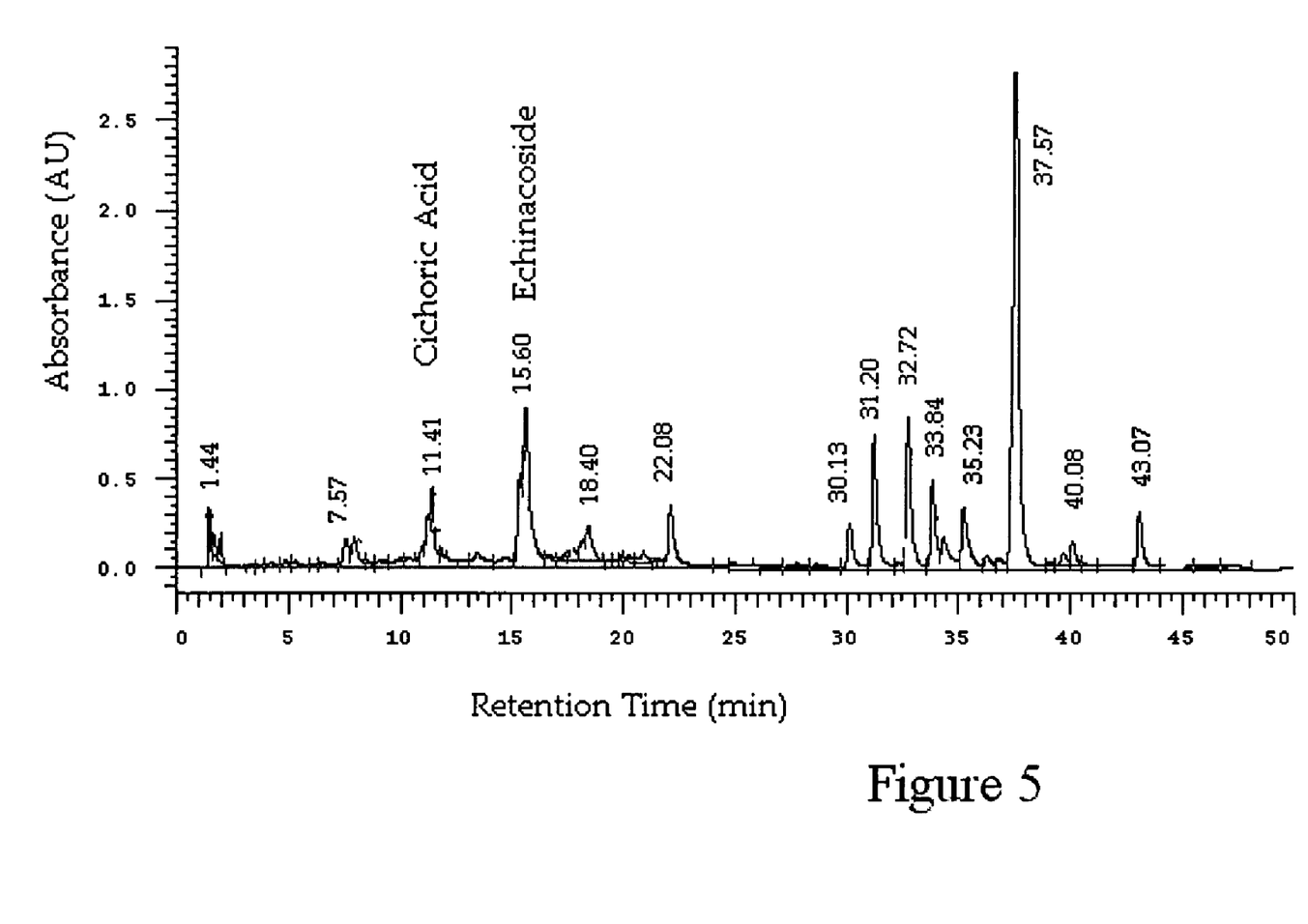
FIG. 5 is a HPLC profile of a 70 percent ethanol extract of a mixture of *Echinacea angustifolia* root, and *Echinacea purpurea* root, stem, leaves and flower head.

The extract was analyzed by high pressure liquid chromatography (HPLC) and the chromatogram is shown in FIG. 5. Retention times of the various compounds were: echinacoside at 11.41 min; cichoric acid at 15.60 min; Dodeca-2E,4E,8Z, 10E-tetraenoic acid isobutylamide and Dodeca-2E,4E,8Z, 10Z-tetraenoic acid isobutylamide at 37.51 min. The HPLC chromatogram of the alcohol extraction method outlined in Comparative Example 1 illustrates that this method results in the extraction of not only immunosuppressive compounds but also immunostimulatory compounds as indicated by the presence of echinacoside and cichoric acid at 11.41 min and 15.60 min respectively, in addition to the lipophilic compounds such as Dodeca-2E,4E,8Z,10E-tetraenoic acid isobutylamide and Dodeca-2E,4E,8Z, 10Z-tetraenoic acid isobutylamide observed at a retention time of 37.51 min.

Comparative Example 2

Nine kilograms of dry *Echinacea angustifolia* and *Echinace purpurea* roots with 12 percent moisture were ground in hammer mill and the ground root transferred to an extractor. Thirty-six liters of 70 percent ethanol were added. The extractor was heated to 40° C. and extraction solvent circulated for 3 hours. The liquid was collected from the extractor and the root material removed and placed into a hydraulic press in order to obtain any remaining liquid. The liquid from the press was combined with the liquid collected from the extractor. The combined liquid was then filtered first through 100 µm screen and then a 10 µm screen. The total volume of the filtrate was 32 L. The filtrate was condensed at 40° C. under reduced pressure to remove most of the ethanol. Five liters of concentrate was obtained.

Figure 6:
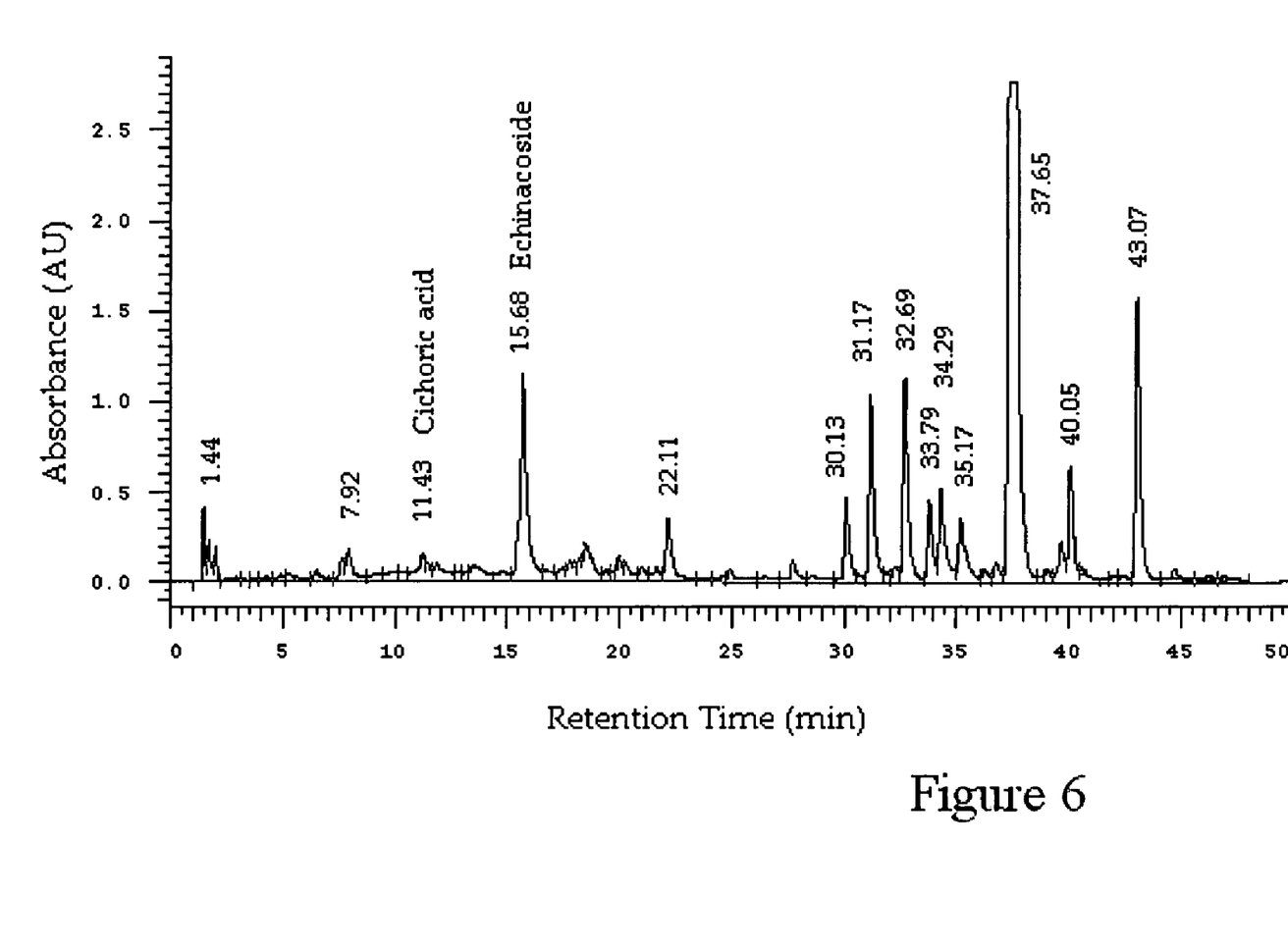
FIG. 6 is a HPLC profile of 70 percent ethanol extract of a mixture of *Echinacea angustifolia* root and *Echinacea purpurea* root.

The extract was analyzed by high pressure liquid chromatography (HPLC) and the chromatogram is shown in FIG. 6. The retention times of the various compounds were: echinacoside at 11.50 min; cichoric acid at 15.68 min; Dodeca-2E, 4E,8Z, 10E-tetraenoic acid isobutylamide and Dodeca-2E, 4E,8Z, 10Z-tetraenoic acid isobutylamide at 37.71 min. The HPLC chromatogram of the alcohol extraction method outlined in Comparative Example 2 illustrates that this method results in the extraction of not only immunosuppressive compounds but also immunostimulatory compounds as indicated by the presence of echinacoside and cichoric acid at 11.50 min and 15.68 min, respectively, in addition to the lipophilic compounds such as Dodeca-2E,4E,8Z,10E-tetraenoic acid isobutylamide and Dodeca-2E,4E,8Z, 10Z-tetraenoic acid isobutylamide observed at a retention time of 37.71 min.

Comparative Example 3

Figure 7:
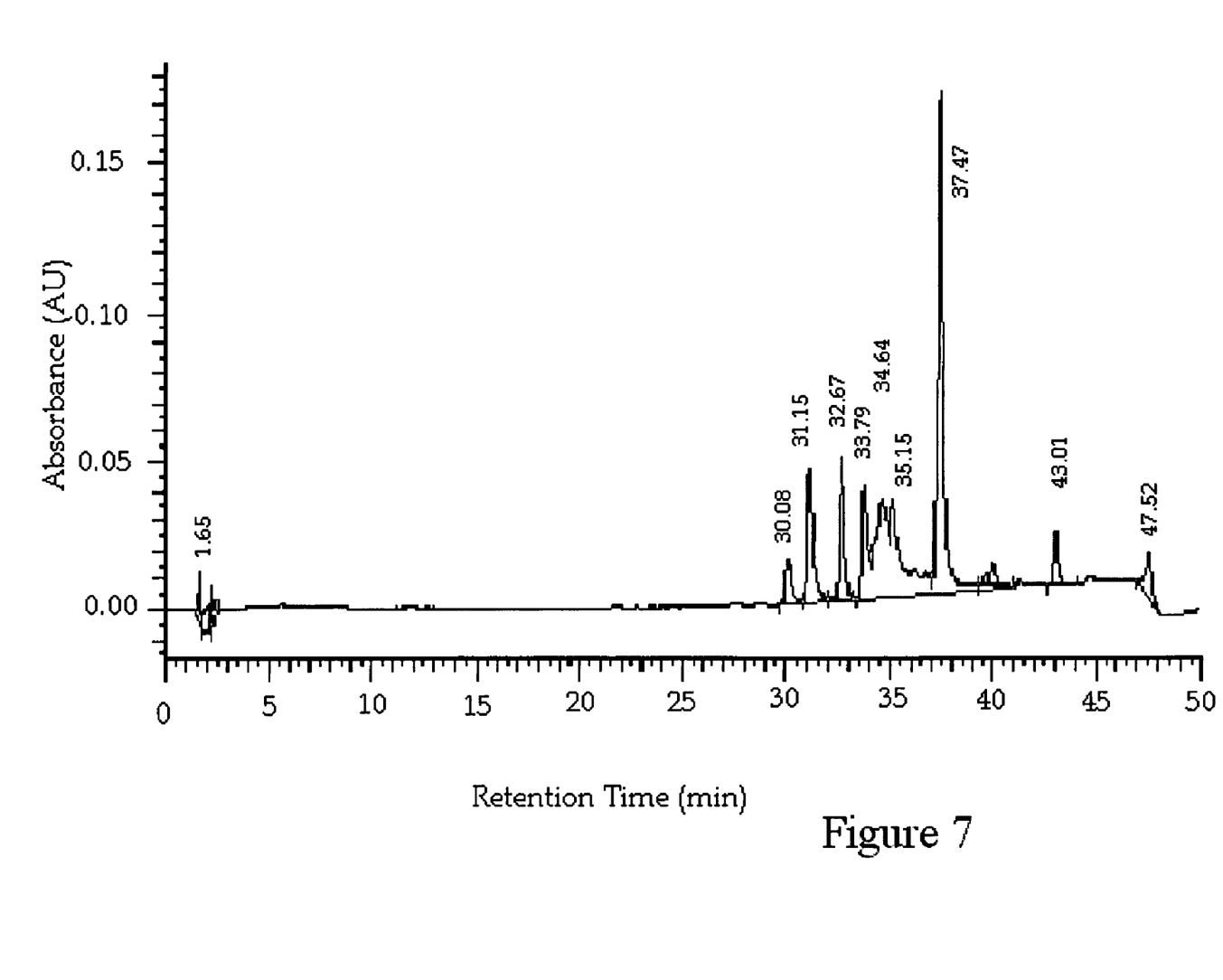
FIG. 7 is a HPLC profile of a commercial *Echinacea* product shown to contain both hydrophilic and lipophilic components.

High pressure liquid chromatography was used to analyze the contents of a commercial product containing *Echinacea purpurea* root, and *Echinacea angustifolia* root. The HPLC profile is shown in FIG. 7 The retention times of the various compounds were: echinacoside at 11.44 min; cichoric acid at 15.49 min; Dodeca-2E,4E,8Z, 10E-tetraenoic acid isobutylamide and Dodeca-2E,4E,8Z, 10Z-tetraenoic acid isobutylamide at 37.65 min.

Figure 8:
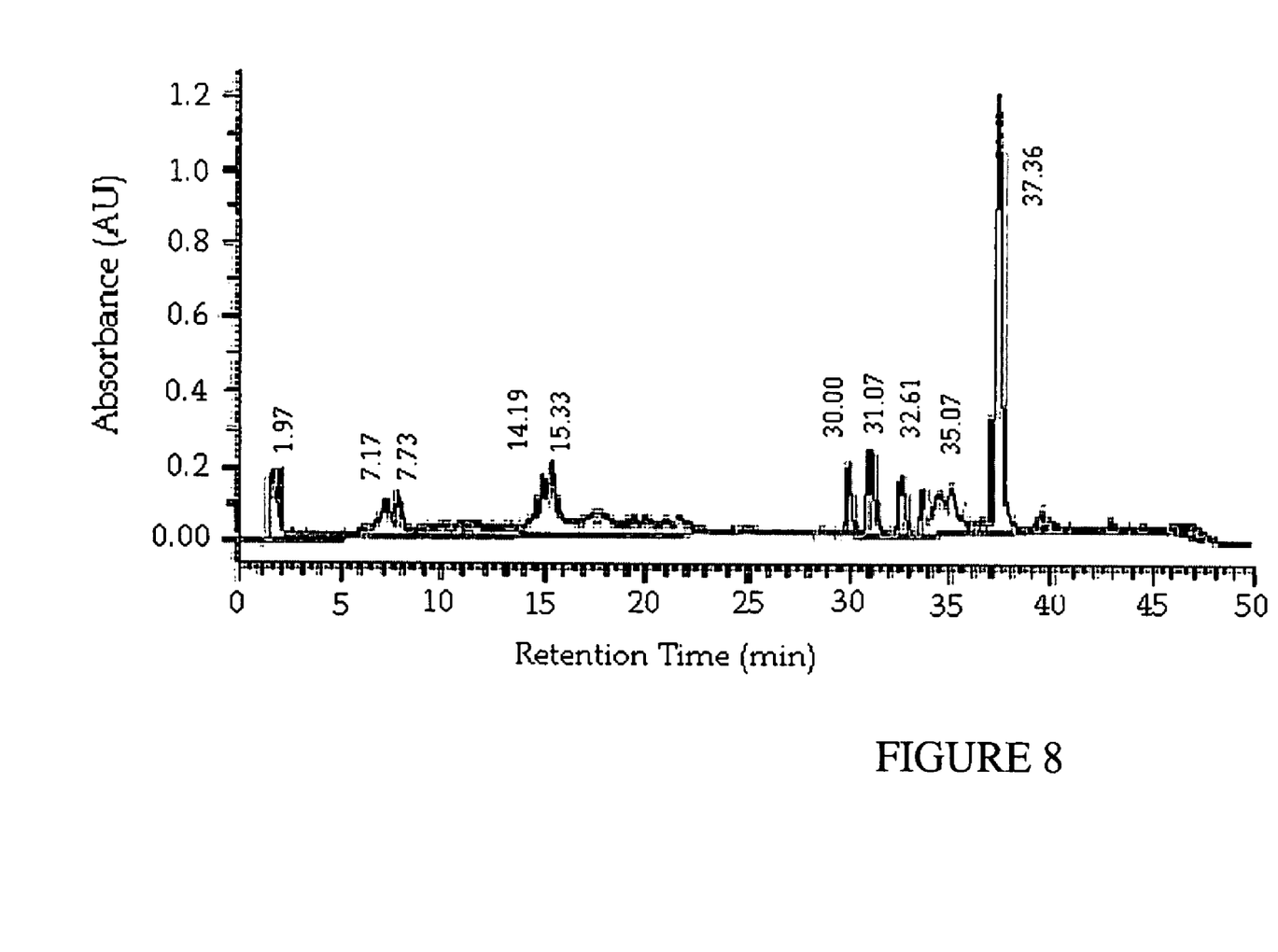
FIG. 8 is a HPLC profile of a commercial *Echinacea* product shown to contain both hydrophilic and lipophilic components.

The commercial product analyzed in FIG. 8 contained fresh *Echinacea* root juice, and fresh *Echinacea* leaf juice, flower juice and mature *Echinacea* seed. High pressure liquid chromatography was used to analyze the contents of the marker compounds. The retention times of the various compounds were: echinacoside at 11.23 min; cichoric acid at 15.33 min; Dodeca-2E,4E,8Z, 10E-tetraenoic acid isobutylamide and Dodeca-2E,4E,8Z, 10Z-tetraenoic acid isobutylamide at 37.36 min.

The HPLC chromatograms of the commercial products illustrates that these products contain not only immunosuppressive compounds but also immunostimulatory compounds as indicated by the presence in both chromatograms of echinacoside and cichoric acid peaks at retention times of about 11.50 min and 15 min, respectively, in addition to the hydrophilic compounds such as Dodeca-2E,4E,8Z,10E-tetraenoic acid isobutylamide and Dodeca-2E,4E,8Z, 10Z-tetraenoic acid isobutylamide observed at a retention time of 37.36 min.

The foregoing is illustrative of the present invention, and is not to be construed as limiting thereof. The invention is defined by the following claims, with equivalents of the claims to be included therein.

What is claimed is:

1. A process for isolating immunosuppressive alkamides from *Echinacea* plant material comprising the steps of:
    (a) extracting *Echinacea* plant material with an alcohol to provide an *Echinacea* concentrate;
    (b) extracting the *Echinacea* concentrate with olive oil to provide a lipophilic fraction containing immunosuppressive alkamides and a hydrophilic fraction; and
    (c) separating the hydrophilic fraction from the lipophilic fraction and further extracting the lipophilic fraction with water to remove any hydrophilic components in the lipophilic fraction and to provide a remaining lipophilic fraction having a concentration of *Echinacea* immunosuppressive alkamides from 0.5 percent to 50 percent w/w.

2. The process of claim 1, wherein the *Echinacea* plant material is selected from the group consisting of *Echinacea angustifolia, Echinacea purpurea, Echinacea pallida, Echinacea atrorubens, Echinacea laevigata, Echinacea sanguinea, Echinacea simulata,* and *Echinacea tennesseensis.*

3. The process of claim 1, wherein the alcohol is selected from the group consisting of ethanol, methanol, and isopropanol.

4. The process of claim 1, wherein the water is selected from the group consisting of deionized water, spring water, distilled water, tap water and well water.

5. A process for isolating immunosuppressive alkamides from *Echinacea* plant material comprising the steps of:
    (a) extracting *Echinacea* plant material with an alcohol to provide an *Echinacea* concentrate;
    (b) extracting the *Echinacea* concentrate with vegetable oil or lecithin to provide a lipophilic fraction containing immunosuppressive alkamides and a hydrophilic fraction; and
    (c) separating the hydrophilic fraction from the lipophilic fraction and further extracting the lipophilic fraction with water to remove any hydrophilic components in the lipophilic fraction and to provide a remaining lipophilic fraction having a concentration of *Echinacea* immunosuppressive alkamides from 0.5 percent to 50 percent w/w.

6. The process of claim 5, wherein the *Echinacea* plant material is selected from the group consisting of *Echinacea angustifolia, Echinacea purpurea, Echinacea pallida, Echinacea atrorubens, Echinacea laevigata, Echinacea sanguinea, Echinacea simiulata*, and *Echinacea tennesseensis*.

7. The process of claim 5, wherein the alcohol is selected from the group consisting of ethanol, methanol, and isopropanol.

8. The process of claim 5, wherein the water is selected from the group consisting of deionized water, spring water, distilled water, tap water, and well water.

* * * * *